United States Patent [19]

Poss et al.

[11] Patent Number: 5,208,212

[45] Date of Patent: May 4, 1993

[54] HERBICIDAL COMPOSITIONS CONTAINING TRIAZOLINONES

[75] Inventors: Kathleen M. Poss, Lawrenceville, N.J.; Frederick W. Hotzman, Morrisville, Pa.; Jacques Meyer, Zofingen, Switzerland

[73] Assignee: FMC Corporation, Philadelphia, Pa.

[21] Appl. No.: 969,648

[22] Filed: Oct. 30, 1992

Related U.S. Application Data

[60] Continuation-in-part of Ser. No. 852,424, Mar. 16, 1992, which is a division of Ser. No. 664,704, Mar. 5, 1991, Pat. No. 5,125,958, which is a continuation-in-part of Ser. No. 462,360, Dec. 28, 1989, abandoned, which is a continuation-in-part of Ser. No. 383,109, Jul. 20, 1989, abandoned, which is a continuation-in-part of Ser. No. 238,804, Aug. 31, 1988, abandoned.

[51] Int. Cl.$^5$ .................. A01N 43/653; A01N 39/02; A01N 39/04
[52] U.S. Cl. ................... 504/139; 504/134; 504/136
[58] Field of Search ............ 504/139, 145, 146

[56] References Cited

U.S. PATENT DOCUMENTS

| | | | |
|---|---|---|---|
| 4,213,773 | 7/1980 | Wolf | 71/92 |
| 4,318,731 | 3/1982 | Kajioka et al. | 71/92 |
| 4,398,943 | 8/1983 | Kajioka et al. | 71/92 |
| 4,404,019 | 9/1988 | Uematsu et al. | 71/92 |
| 4,439,229 | 3/1984 | Swithenbank | 71/96 |

FOREIGN PATENT DOCUMENTS

| | | |
|---|---|---|
| 68822 | 1/1983 | European Pat. Off. |
| 3603789A1 | 8/1987 | Fed. Rep. of Germany |
| 56-53662 | 5/1981 | Japan |
| 58-225070 | 12/1983 | Japan |
| 2090250 | 7/1982 | United Kingdom |

OTHER PUBLICATIONS

PCT International Application No. WO 86/04481, published Aug. 14, 1986.
PCT International Application No. WO 85/04307, published Oct. 10, 1985.
PCT International Application No. WO 85/01637, published Apr. 25, 1985.
PCT International Application No. WO 86/02642, published May 9, 1986.
PCT International Application No. 87/00730, published Feb. 12, 1987.
PCT International Application No. WO 85/01939, published May 9, 1985.
Derwent Abstract, Accession No. 85-100678, 1985.
Derwent Abstract, Accession No. 84-090015, 1984.
Derwent Abstract, Accession No. 25467K, 1983.
Derwent Abstract, Accession No. 88-316,199 1988.
Derwent Abstract, Accession No. 87-001,569, 1987.
Derwent Abstract, Accession No. 87-229,899, 1987.
Derwent Abstract, Accession No. 88-184,132 1988.
Derwent Abstract, Accession No. 88-127,035 1988.
Derwent Abstract, Accession No. 87-362,698 1987.
Derwent Abstract, Accession No. 88-063,985 1988.
Derwent Abstract, Accession No. 85-122,460 1985.
Derwent Abstract, Accession No. 86-020,889 1986.
Derwent Abstract, Accession No. 87-183,175, 1987.
Derwent Abstract, Accession No. 84-020,128 1984.
Derwent Abstract, Accession No. 84,254,501, 1984.
Derwent Abstract, Accession No. 86-133,830, 1986.
Derwent Abstract, Accession No. 86-133,831, 1986.
Derwent Abstract, Accession No. 88-088,439, 1988.
Derwent Abstract, Accession No. 88-025,708, 1988.
Derwent Abstract, Accession No. 86-133,827, 1986.
Derwent Abstract, Accession No. 84-246,947, 1984.
Derwent Abstract, Accession No. 7605J, 1982.
Derwent Abstract, Accession No. 85-181,185, 1985.
Derwent Abstract, Accession No. 44794T, 1971.
Derwent Abstract, Accession No. 88-072,656, 1988.
PCT International Application No. 87/07602, published Dec. 17, 1987.
Chemical Abstract 105(7):60524v, 1986.

*Primary Examiner*—Richard L. Raymond
*Assistant Examiner*—B. Bembenick
*Attorney, Agent, or Firm*—Stanford M. Back; Norman L. Craig; Robert M. Kennedy

[57] ABSTRACT

This invention relates to compositions comprising 1-aryl-4,5-dihydro-1,2,4-triazol-5(1H)-ones (triazolinones) in combination with the herbicide (2,4-dichlorophenoxy)acetic acid (2,4-D), or like substituted phenoxyalkanoic acids, or esters, or alkali metal or ammonium salts thereof; or with certain herbicidal sulfonylureas, or mixtures of these classes of compounds, to provide herbicidal compositions which are highly effective against a broad array of crop weeds, particularly broadleaf weeds, in crops such as wheat.

12 Claims, No Drawings

HERBICIDAL COMPOSITIONS CONTAINING TRIAZOLINONES

This application is a continuation-in-part of application Ser. No. 852,424, filed Mar. 16, 1992, which in turn is a divisional of Ser. No. 664,704, filed Mar. 5, 1991 (U.S. Pat. No. 5,125,958), which in turn is a continuation-in-part of application Ser. No. 462,360, filed Dec. 28, 1989 (now abandoned), which in turn is a continuation-in-part of application Ser. No. 383,109, filed Jul. 20, 1989 (now abandoned), which in turn is a continuation-in-part of application Ser. No. 238,804, filed Aug. 31, 1988 (now abandoned).

BACKGROUND OF THE INVENTION

This invention relates to compositions comprising 1-aryl-4,5-dihydro-1,2,4-triazol-5(1H)-ones (hereinafter "triazolinones") in combination with other herbicidal compounds, which compositions are useful as herbicides, especially against broadleaf weeds such as mustards, kochia, and the like. More particularly, it relates to these triazolinones in combination with the herbicide (2,4-dichlorophenoxy)acetic acid ("2,4-D"), or like substituted phenoxyalkanoic acids, or herbicidally effective commercially available esters, or alkali metal or ammonium salts thereof; or with certain herbicidal sulfonylureas, as defined below (hereinafter "sulfonylureas"), or mixtures of these classes of compounds, to provide post-emergence herbicidal compositions which are highly effective against a broad array of weeds which infest crops.

The triazolinones employed in this invention, their preparation, and their use in combination with other herbicides including known herbicidal acetamides, benzothiodiazinones, triazines, dinitroanilines, and aryl ureas, is known from PCT International Application WO 90/02120, published Mar. 9, 1990, discussed in further detail below, and whose U.S. counterpart is a parent of the present continuation-in-part application. The combination of these triazolinones with 2,4-D, or other substituted phenoxy alkanoic acids, or with sulfonylureas is, however, not taught or suggested by this PCT publication.

SUMMARY OF THE INVENTION

In accordance with the present invention it has now been found that compositions comprising triazolinones, as defined herein, in combination with 2,4-D, or like herbicidally effective substituted phenoxy alkanoic acids, or with sulfonylureas, or mixtures of the latter compounds, in agriculturally acceptable carriers, are highly effective post-emergence herbicides in the control of a wide number of weeds which infest crops, particularly members of the mustard family, including shepherdspurse, bitter cress, blue mustard, tansymustard, flixweed, and field pennycress.

These compositions are particularly advantageous in that they provide for rapid kill of the majority of plant tissues, protection against the regrowth of the weeds and herbicidal control over a broad spectrum of broadleaf weeds, thus providing overall better herbicidal control. These compositions are generally faster acting or more effective than any one component alone. In the case of 2,4-D, the combination allows the use of lower rate of 2,4-D, compared with a higher application rate of 2,4-D alone.

DETAILED DESCRIPTION OF THE INVENTION

As described in PCT application WO 90/02120 (supra), which is incorporated herein by reference, the triazolinones employed as components of the claimed compositions comprise herbicidal 1-aryl-4,5-dihydro-2,4-triazol-5(1H)-ones of the formula

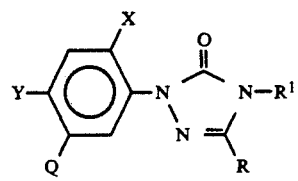

in which

R is halogen or lower alkyl;

$R^1$ is haloalkyl;

X is hydrogen, halogen, alkyl, haloalkyl, alkoxy or nitro;

Y is hydrogen, halogen, alkyl, alkoxy, haloalkyl, halo lower alkylsulfinyl, or halo lower alkoxy;

Q is $-CH(R^2)C(R^3)(R^4)Q'$ or $-CH=C(R^4)Q'$;

$R^2$ is H or halogen;

$R^3$ is halogen;

$R^4$ is H or lower alkyl;

Q' is $CO_2H$, $CO_2R^5$, $CON(R^6)(R^7)$, CN, CHO, or $C(O)R^5$;

$R^5$ is alkyl, alkoxycarbonylalkyl, cycloalkyl, benzyl, chlorobenzyl, alkylbenzyl, or haloalkylbenzyl; and each of $R^6$ and $R^7$ is independently H, or a radical which is an alkyl, cycloalkyl, alkenyl, alkynyl, alkoxy, phenyl, benzyl, or $SO_2R^6$ (in which $R^6$ is other than H) or is one of said radicals substituted by halogen, alkyl, or cyano;

or a base-addition salt of the compound in which Q' is $CO_2H$; or resolved isomers thereof; with the proviso that any alkyl, alkenyl, or alkynyl moiety have less than 6 carbon atoms and that any cycloalkyl moiety have 3 to 7 carbon atoms.

Preferred amongst these compounds where $R^2$, $R^3$ and $R^4$ have the meanings set forth above, and R, R', X and Y may be as follows: each of R and $R^1$ may, independently, be lower alkyl (preferably methyl) or halo lower alkyl such as fluoro lower alkyl (e.g. $CF_2CHF_2$ or $CHF_2$). R may also be a halogen atom such as chlorine. Preferably R is methyl and $R^1$ is $CHF_2$. The substituent X may be hydrogen; halogen such as chlorine, bromine, or fluorine (preferably fluorine); alkyl such as lower alkyl (e.g. methyl); haloalkyl such as halo lower alkyl (e.g. $CF_3$, $CH_2F$ or $CHF_2$); alkoxy such as lower alkoxy (e.g. methoxy); or nitro; and Y may be hydrogen; halogen such as chlorine, bromine, or fluorine (preferably bromine or chlorine); alkyl such as lower alkyl (e.g. methyl); alkoxy such as lower alkoxy (e.g. methoxy); haloalkyl such as halo lower alkyl (e.g. fluoroalkyl); halo lower alkylsulfinyl (e.g. $-SOCF_3$); or halo lower alkoxy (e.g. $-OCHF_2$). Particularly preferred X, Y substituents are: 2-F, 4-Cl; 2-F, 4-Br; 2,4-diCl; 2-Br, 4-Cl; and 2-F, 4-$CF_3$.

It is preferable that any alkyl, alkenyl, alkynyl or alkylene moiety (such as the hydrocarbon moiety of an alkoxy or haloalkoxy group) have less than 6 carbon atoms, e.g. 1 to 3 or 4 carbon atoms, and that any cycloalkyl moiety have 3 to 7 ring carbon atoms, preferably 3–6 carbon atoms.

Any acidic compounds, including sulfonamides in which $NR^6R^7$ is $NHSO_2R^6$, may be converted to the corresponding base addition salt by known methods.

Of particular interest in this invention are such compounds as ethyl 2-chloro-3-[2-chloro-4-fluoro-5-(4-difluoromethyl-4,5-dihydro-3-methyl-5-oxo-1H-1,2,4-triazol-1-yl)phenyl]propionate, (hereinafter "Compound P") having the formula

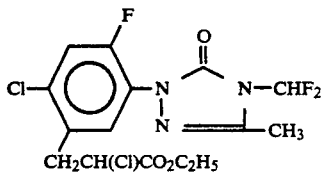

and, e.g., the 4-chloro analog of this 4-fluoro compound.

Certain of the 1-aryl-4,5-dihydro-1,2,4-triazol-5(1H)-ones of the present invention contain an asymmetric carbon atom; the invention thus includes individual stereoisomers as well as racemic and non-racemic mixtures of the instant compounds. For example, ethyl 2-chloro-3-[2-chloro-4-fluoro-5-(4-difluoromethyl-4,5-dihydro-3-methyl-5-oxo-1H-1,2,4-triazol-1-yl)phenyl]propionate ("Compound P") is composed of a 2S and a 2R isomer. The 2S and 2R isomers of Compound P were separated by High Pressure Liquid Chromatography (HPLC), a method known to one skilled in the art, using a DIACEL CHIRALCEL OD column (distributed by Diacel Chemical Industries Ltd., Exton, Pa.), 4.6 mm ID×250 mm, packed with silica gel of 10 μm in particle size. Elution was accomplished with 1.5% ethanol in hexane at a flow rate of 1 mL/minute.

The triazolinone compounds may be prepared by methods described in PCT Application WO/02120 or in the following illustrative example, or by methods analogous and similar thereto which are within the skill of the art.

For instance, in Step A of the example below an amino compound of the formula (II)

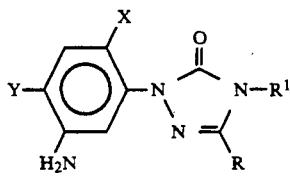

(such as the compound shown in Example 1 of International patent publication WO 87/03782, published Jul. 2, 1987) is reacted (according to the Meerwein arylation reaction described below or a modification thereof) with an olefinic compound having the formula $CHR^2=CR^4Q'$ to form a compound of Formula I above in which Q is $-CH(R^2)C(R^3)(R^4)Q'$ and in which $R^3$ is halogen. In this type of reaction the amino compound is converted to a diazonium salt which then reacts with the olefinic compound through a radical mechanism. The Meerwein arylation reaction is discussed in an article by Doyle et al in J. Org. Chem., 42, 2431 (1977) which also describes a modification of that reaction in which an alkyl nitrite and a copper (II) halide are employed. (Step A of the example below employs the Doyle et al modification.) Instead, one may employ the unmodified reaction, in which the arenediazonium halide is initially prepared in an aqueous halogen acid solution and then mixed with the olefinic compound in the presence of an appropriate solvent (e.g. acetone) followed by the copper salt, such as copper (I) chloride.

Examples of olefinic compounds having the formula $CHR^2=CR^4Q'$ are methyl acrylate, ethyl acrylate, methyl methacrylate, methyl crotonate, methyl 3-chloroacrylate, methacrolein, vinyl methyl ketone, methacrylonitrile and acrylamide.

The product made by the reactions described above, i.e. a compound of Formula I in which Q is $-CH(R^2)C(R^3)(R^4)Q'$ and in which $R^3$ is halogen, may be treated to form other compounds of this invention. Dehydrohalogenation of that compound (e.g. with sodium hydride or other suitable base), when $R^2$ is H, yields a compound in which Q is $-CH=C(R^4)Q'$ (as in Step B of the example). That compound may be hydrogenated or halogenated to form a compound in which Q is $-CH(R^2)C(R^3)(R^4)Q'$ and $R^3$ is H (from hydrogenation, as in Step C) or $R^2$ and $R^3$ are halogen. When Q' is $-CO_2H$, the acidic compound of formula I may be converted to the corresponding amide, as by first treating with a reagent such as thionyl chloride to form the acid halide (wherein Q' is, for example, $-COCl$) and then reacting with ammonia or an amine. Alternative methods of amide formation, involving carbodiimide-mediated coupling, are known, as for example where the amide is formed from the carboxylic acid (of e.g. formula I) and the amine, in the presence of dicyclohexylcarbodiimide, I-hydroxybenzotriazole and a base such as a tertiary amine, e.g. N,N-diisopropylethylamine or triethylamine, in a solvent such as tetrahydrofuran.

Instead of starting with an amino compound one may start with an otherwise identical compound having a CHO group in place of the NH2 group and react it with a Wittig reagent (which may be a standard type of Wittig reagent or a modified type such as a Wadsworth-Emmons reagent). Thus, the reagent may be an alkylidene phosphorane whose alkylidene group has the formula $=C(R^4)Q'$ such as $(C_6H_5)_3P=CHCO_2R_5$ or it may be a phosphonate ylide comprising a phosphonate diester in which the group directly attached to the P atom has the formula $-CH(R^4)Q$ such as $(C_2H_5O)_2$-$P(O)CH_2CO_2R^5$, used together with, say, NaH in known manner. $R^5$ is preferably lower alkyl such as methyl or ethyl. The product thereof may be hydrogenated to produce a compound of Formula I in which $R^2$ and $R^3$ are each hydrogen, or it may be halogenated (e.g. with chlorine) to form a compound of Formula I in which $R^2$ and $R^3$ are each halogen. The latter compound may in turn be dehydrohalogenated to form a compound in which $R^4$ is halogen and then hydrogenated to form a compound of Formula I in which $R^4$ is halogen and $R^3$ and $R^2$ are H.

Instead of starting with a compound containing the triazolinone ring and adding thereto the Q substituent, one may start with a compound of the formula

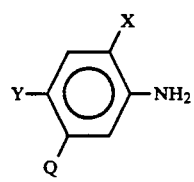

and then form the triazolinone ring. Compounds of Formula III are shown, for instance, in published European patent applications 300387 and 300398. The NH$_2$ group may be converted to a triazolinone ring in known manner. For instance it may be converted to an NHNH$_2$ (i.e. hydrazine) group in the conventional fashion, by diazotization followed by reduction with sodium sulfite, and the hydrazine group may be converted to a triazolinone ring.

When X and Y are substituents other than H, such substituents may be introduced at various stages of the process, e.g., prior to the formation of a compound containing the Q substituent. One or both of these substituents may be introduced after the introduction of the Q substituent; for instance, a chlorine substituent on the benzene ring may be introduced during one of the halogenation steps which modify the Q substituent, as described above.

The preparation of the triazolinone components is illustrated by the following example. In this application, all parts are by weight and all temperatures are in °C. unless otherwise indicated.

EXAMPLE

Methyl 3-[2,4-Dichloro-5-(4-Difluoromethyl-4,5-Dihydro 3-Methyl-5-Oxo-1H-1,2,4-Triazol-1-Yl)Phenyl]Propionate Step A: Methyl 2-Chloro-3-[2,4-dichloro-5-(4-difluoromethyl-4,5-dihydro-3-methyl-5-oxo-1H-1,2,4-triazol-1-yl)phenyl]propionate To a cold (0° C.), stirred mixture of 28.7 g (0.333 mole) of methyl acrylate, 2.51 g (0.0244 mole) of tert-butyl nitrite, and 2.6 g (0.019 mole) of copper (II) chloride in 50 mL of acetonitrile was added dropwise a solution of 5.0 g (0.016 mole) of 1-(5-amino-2,4-dichlorophenyl)-4-difluoromethyl-4,5-dihydro-3-methyl-1,2,4-triazol-5(1H)-one in 15 mL of acetonitrile. After complete addition the reaction mixture was allowed to warm to room temperature and was stirred for approximately 18 hours. The reaction mixture was diluted with 15 mL of 2N hydrochloric acid solution. The mixture was extracted with four portions of diethyl ether. The combined extracts were dried over anhydrous magnesium sulfate, filtered, and the filtrate evaporated under reduced pressure to give an oil. The oil was purified by column chromatography on silica gel, eluting with n-heptane:ethyl acetate (4:1) to give 5.0 g of methyl 2-chloro-3-[2,4-dichloro-5-(4-difluoromethyl-4,5-dihydro-3-methyl-5-oxo-1H-1,2,4-triazol-1-yl)phenyl]propionate as an oil.

Step B Methyl 3-[2,4-dichloro-5-(4-difluoromethyl-4,5-dihydro-3-methyl-5-oxo-1H-1,2,4-triazol-1-yl)phenyl]-2-propenoate To a stirred, cold (0° C.) solution of 4.16 g (0.0100 mole) of methyl 2-chloro-3-[2,4-dichloro-5-(4-difluoromethyl-4,5-dihydro-3-methyl-5-oxo-1H-1,2,4 -triazol-1-yl)phenyl]propionate in 15 mL of N,N-dimethylformamide was added portionwise 0.29 g (0.012 mole) of sodium hydride. After complete addition the reaction mixture was allowed to warm to room temperature and was stirred for 30 minutes. The reaction mixture was heated at 60° C. for six hours, then was stirred at room temperature for approximately 18 hours. The reaction mixture was poured into ice water, and the resultant aqueous mixture was extracted with four portions of diethyl ether. The extracts were combined and washed successively with water and an aqueous, saturated sodium chloride solution. The washed organic phase was dried over anhydrous magnesium sulfate and was filtered. The filtrate was evaporated under reduced pressure to give a white foam. The foam was purified by column chromatography on silica gel, eluting with n-heptane:ethyl acetate (4:1), to give 1.63 g of methyl 3-[2,4-dichloro-5-(4-difluoromethyl-4,5-dihydro-3-methyl-5-oxo-1H-1,2,4-triazol-1-yl)phenyl]-2-propenoate as a solid, m.p. 141°-151° C.

Step C: Methyl 3-[2,4-dichloro-5-(4-difluoromethyl-4,5-dihydro-3-methyl-5-oxo-1H-1,2,4-triazol-1-yl)phenyl]propionate Hydrogenation of 0.59 g (0.0016 mole) of methyl 3-[2,4-dichloro-5-(4-difluoromethyl-4,5-dihydro-3-methyl-5-oxo-1H-1,2,4-triazol-1-yl)phenyl]-2-propenoate over approximately 0.2 g (0.0009 mole) of platinum (IV) oxide in approximately 15 mL of ethyl acetate gave 0.59 g of methyl 3-[2,4-dichloro-5-(4-difluoromethyl-4,5-dihydro-3-methyl-5-oxo-1H-1,2,4-triazol-I-yl)phenyl]propionate as a clear oil, which crystallized upon standing. The crystals were triturated with petroleum ether and recovered by filtration, m.p. 70°-73° C.

The preferred triazolinone component of the compositions of this invention as stated above, namely ethyl 2-chloro-3-[2-chloro-4-fluoro-5-(4-difluoromethyl-4,5-dihydro-3-methyl-5-oxo-(1H)-1,2,4-triazol-1yl)phenyl]-propionate, (i.e., "Compound P") may readily be prepared in accordance with the procedures of the foregoing example, but substituting 1-(5-amino-4-chloro2-fluorophenyl)-4-difluoromethyl-4,5-dihydro-3-methyl1,2,4-triazol-5-(1H)-one and ethyl acrylate for 1-(5 -amino-2,4-dichlorophenyl)-4-difluoromethyl-4,5-dihydro-3-methyl-1,2,4-triazol-5(1H)-one and methyl acrylate in Step A.

As stated above, the second component of the herbicidal triazolinone composition of this invention is preferably a chlorinated phenoxy lower alkanoic acid compound, and most particularly (2,4-dichlorophenoxy)acetic acid, commonly known as 2,4-D, and the esters, or alkali metal or ammonium salts thereof, all of which are available commercially from several sources, e.g. Chevron (Weed-B-Gone ™), Pennwalt (Pennamine ™ D), and the like. However, there may also be employed related, commercially available herbicidal chlorinated lower alkylphenoxy alkanoic acid compounds as (4-chloro-2-methylphenoxy)acetic acid, commonly known as MCPA; 4-(4-chloro-2-methylphenoxy)butanoic acid, commonly known as MCPB; 2-(4-chloro-2-methylphenoxy)propionic acid, commonly known as MCPP or mecoprop, and its herbicidally active isomers; and the esters, salts, and amines of each of the above, such as MCPA amine, or MCPA ester, (Riverdale Chemical Co., Glenwood, Illinois), MCPP-p (BASF), or the like.

By the term esters, as used above to define 2,4-D and related phenoxy alkanoic acid derivatives, is meant principally those prepared from $C_1$-$C_{10}$ aliphatic alcohols. Of these, the isooctyl ester of 2,4-D, which is commercially available as Weedtime II ("2,4-D ester") from Applied Biochemists Inc. (Mequon, Wis.), is preferred. The corresponding salts are generally alkali metal or ammonium salts, commercially available as, e.g., the potassium salt, or as the ammonium salt, (commonly referred to as "amines" of 2,4-D compounds), e.g., the dimethylamine salt. (See, e.g., Farm Chemicals Handbook, Meister Publishing Co. (1990), pp. C-87-88.) The compound MCPP-p, set forth above, is the resolved (+) isomer of the above-defined commercially available mecoprop. (See Farm Chemicals Handbook, supra, pp. C-183-185.).

Alternatively, in a further embodiment of this invention, the triazolinones may instead be combined with herbicidal sulfonylureas of the formula

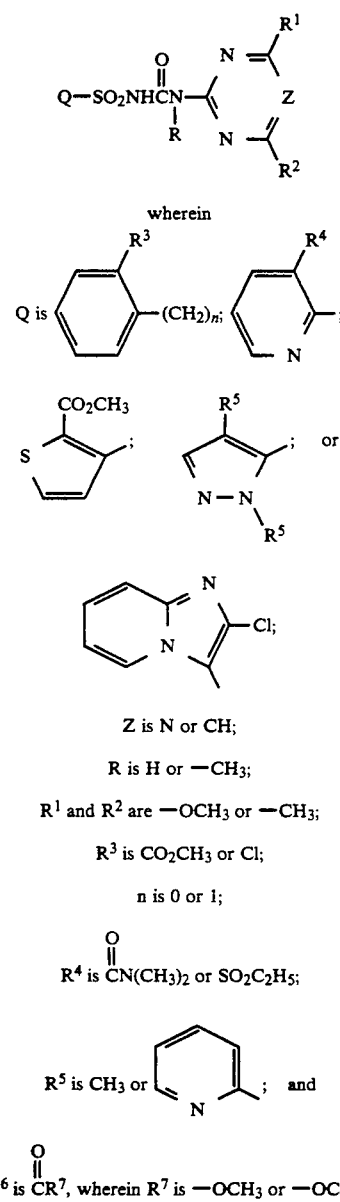

wherein

Q is

Z is N or CH;

R is H or —CH$_3$;

R$^1$ and R$^2$ are —OCH$_3$ or —CH$_3$;

R$^3$ is CO$_2$CH$_3$ or Cl;

n is 0 or 1;

R$^4$ is $\overset{O}{\underset{\|}{C}}$N(CH$_3$)$_2$ or SO$_2$C$_2$H$_5$;

R$^5$ is CH$_3$ or [pyridinyl]; and

R$^6$ is $\overset{O}{\underset{\|}{C}}$R$^7$, wherein R$^7$ is —OCH$_3$ or —OC$_2$H$_5$.

Included amongst the sulfonylureas which, in accordance with this invention, may be used in combination with the herbicidal triazolinones are known commercially available herbicides such as:

methyl 2-[[[[(4-methoxy-6-methyl-1,3,5-triazin-2-yl)amino]carbonyl]amino]sulfonyl]benzoate (metsulfuronmethyl), (ALLY ™ - E. I. DuPont, Wilmington, Del.);

2-chloro-N-[[(4-methoxy-6-methyl-1,3,5-triazin-2-yl)amino]carbonyl]benzenesulfonamide (chlorsulfuron), (GLEAN ™ - E. I. DuPont, Wilmington, Del.);

methyl 2-[[[[[(4,6-dimethoxy-2-pyrimidinyl)amino]-carbonyl]amino]sulfonyl]methyl]]benzoate (bensulfuronmethyl), (LONDAX ™ - E. I. DuPont, Wilmington, Del.);

methyl 2-[[[[N-(4-methoxy-6-methyl-1,3,5-triazin-2-yl)methylamino]carbonyl]amino]sulfonyl]benzoate (tribenuron-methyl), (EXPRESS ™ - E. I. DuPont, Wilmington, Del.);

methyl 3-[[[[(4-methoxy-6-methyl-1,3,5-triazin-2-yl)amino]carbonyl]amino]sulfonyl]-2-thiophenecarboxylate (thifensulfuron-methyl), (HARMONY ™ - E. I. DuPont, Wilmington, Del.);

ethyl 5-[[[[(4,6-dimethoxy-2-pyrimidinyl)amino]-C>carbonyl]amino]sulfonyl]-1-methyl-1H-pyrazole-4carboxylate (pyrazosulfuron-ethyl), (SIRIUS - Nissan Chemical Industries, Ltd., Tokyo, Japan);

2-[[[[(4,6-dimethoxy-2-pyrimidinyl)amino]-carbonyl]amino]sulfonyl]-N,N-dimethyl-3-pyridinecarboxamide (nicosulfuron), (ACCENT ™ - E. I. DuPont, Wilmington, Del.);

methyl 5-[[[[(4,6-dimethyl-2-pyrimidinyl)amino]-carbonyl]amino]sulfonyl]-1-(2-pyridinyl)-1H-pyrazole-4carboxylate (NC-330, - available from Nissan Chemical Industries, Ltd., Tokyo, Japan);

3-ethylsulfonyl-N-[[(4,6-dimethoxy-2-pyrimidinyl)amino]-carbonyl]-2-pyridinylsulfonamide (DPXE 9636, - available from E. I. DuPont Co., Wilmington, Del.); and N-[[(4,6-dimethoxy-2-pyrimidinyl)amino]carbonyl]-2-chloroimidazo-[1,2-a]pyridinecarboxamide (TH-913, - available from Takeda Chemical Industries, Ltd., Tokyo, Japan).

The active herbicidal compositions of this invention may also be used in combination with other herbicides, e.g. they may be mixed with, say, an equal or larger amount of known herbicides such as N-(1-ethylpropyl)-2,4-dinitro-3,4-xylidene (pendamethalin); (RS)-2-[2,4-dichlorophenoxy)phenoxy]propionic acid (diclofop); 2,4-difluoro-2-($\alpha,\alpha,\alpha$-trifluoro-m-tolyloxy)nicotinalanilide (diflufenican); ($\pm$)-2-[4-(6-chloro-1,3-benzoxazol-2yloxy)phenoxy]propionic acid (fenoxaprop); 3-p-cumenyl1,1-dimethylurea (isoproturon); 4-hydroxy-3,5diiodobenzonitrile (ioxynil); or 3,6-dichloro-o-anisic acid (dicamba).

The weight ratio of triazolinone to 2,4-D, or to the sulfonylurea in order to obtain the desired herbicidal effect is not critical, and may be varied widely. Thus, for example, the ratio of triazolinone to 2,4-D may range from about 1:125 to 1:2, more preferably 1:17 to 1:4, while the ratio of triazolinone to sulfonylurea may range from about 8:1 to 30:1, more preferably 1:1 to 16:1. It will be understood that these ranges may be adjusted by those skilled in the art depending upon the crops involved, field conditions and the like.

FORMULATIONS

For herbicidal application, the active compositions are formulated by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compositions may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredients.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal composition and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredients | 40.00 |
| Sodium lignosulfonate | 20.00 |
| Attapulgite clay | 40.00 |
| Total | 100.00 |
| Active ingredients | 90.00 |
| Dioctyl sodium sulfosuccinate | 0.10 |
| Synthetic fine silica | 9.90 |
| Total | 100.00 |
| Active ingredients | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredients | 25.00 |
| Base: | 75.00 |
| 96% hydrated aluminum magnesium silicate | |
| 2% powdered sodium lignosulfonate | |
| 2% powdered anionic sodium alkyl- naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredients may vary according to the manner in which the composition is to be applied, but in general comprise 0.5 to 95% of active ingredient by weight of the herbicidal composition.

The following are specific examples of emulsifiable concentrate formulations:

| Component: | % by Wt. |
|---|---|
| Active ingredients | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredients | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredients | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredients | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surfaceactive agents are available in commerce. The surfaceactive agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

|  | % by Wt. |
|---|---|
| Oil Suspension: | |
| Active ingredients | 25.00 |
| Polyoxyethylene sorbitol hexaoleate | 5.00 |
| Highly aliphatic hydrocarbon oil | 70.00 |
| Total | 100.00 |
| Aqueous Suspension: | |
| Active ingredients | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compositions of this invention may be formulated and/or applied with insecticides, fungicides, nematicides, plant growth regulators, fertilizers, or other agricultural chemicals and may be used as effective soil sterilants as well as selective herbicides in agriculture. In applying an active composition of this invention, whether formulated alone or with other agricultural chemicals, an effective amount and concentration of the active compounds are of course employed; for example, amounts as low as 1 g/ha or less, e.g. 1–125 g/ha, may be employed for control of broadleafed weeds with little or no injury to crops such as maize or wheat. For field use, where there are losses of herbicide, higher application rates (e.g. four times the rates mentioned above) may be employed.

Herbicidal Activity

The test species used in demonstrating the herbicidal postemergence activity of the compositions of this invention are set forth in each of the tables below. These tests were conducted on populations of these species located in fields at various locations in the United States, the United Kingdom or France. The crops were planted; the weeds were either planted or grew naturally at these locations.

Test plots were typically 10.0 ft by 20.0 ft, with 6.7 ft by 20.0 ft treated with a given rate of a herbicide or herbicide combination. (At any given location these were at least three, and most always, four replications of the individual treatments.) Control of the weed species and injury to the crop was assessed on a percent basis, relative to the nearest untreated area. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. This rating system is set forth in the following table, captioned "Herbicide Rating System."

The herbicides were applied to the test area by spraying an aqueous solution or suspension or emulsion of the compound or combination of compounds over the entire designated area. The formulated herbicides were diluted to a concentration appropriate for the desired application rate on the basis of a spraying rate of 20 gallons per acre. Unless otherwise noted, no surfactant or other adjuvant was added to the spray solution.

For example, to treat the four test replicates at a single location with 0.031 lb/acre of Compound P, 1.04 ml of the 2 lb/gal emulsifiable concentrate formulation was mixed with 1500 ml of water. The solution was sprayed through T-Jet Flat Fan 8002E nozzles (T-Jet Spraying Systems TM) at 30 psi pressure.

Applications were typically made when the weed species were 1–3 inches tall. Percent control was rated at various times after application, as shown in the tables below, using the following "Rating System."

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

TABLES

Herbicidal data at selected application rates are given for various compounds of the invention in the tables below. The test compounds are identified in footnotes of the tables.

In Tables I-IX the triazolinone ethyl-2-chloro-3-[2-chloro-4-fluoro-5-(4-difluoromethyl-4,5-dihydro-3-methyl-5-oxo-(1H)-1,2,4-triazol-l-yl)phenyl]propionate (designated in the tables as "Compound P") was employed, but it will be understood that other triazolinones described above may be employed instead.

The other active ingredients of the claimed herbicidal compositions are as identified in the tables.

The scientific names of all the weed species used in these trials are presented in Table X.

In the tables, the tests were carried out using formulations in which Compound P was first admixed with varying amounts of surfactants and aromatic hydrocarbon solvents. These formulations were then applied to various test plants, and at various rates, as indicated in these tables, using the triazolinone Compound P in combination with the other herbicides of this invention, also indicated in these tables.

Examples of two such formulations of Compound P employed herein are as follows:

| Components (50 g/liter) | wt/% |
|---|---|
| Cmpd P (91.1% purity) | 6.06 |
| Emulsifier 1$^a$ | 3.20 |
| Emulsifier 2$^b$ | 3.20 |
| Dispersant$^c$ | 1.60 |
| Aromatic 100 (solvent)$^d$ | 85.94 |
| First Formulation (2 lbs/gal) | |
| Cmpd P (95% purity) | 26.97 |
| Emulsifier 1$^a$ | 1.95 |
| Emulsifier 2$^b$ | 2.60 |
| Dispersant$^c$ | 1.95 |
| Aromatic 100$^d$ | 66.53 |
| Second Formulation (2 lbs/gal) | |
| Cpmd P (91.4% purity) | 24.42 |
| Emulsifier 1$^a$ | 3.50 |
| Emulsifier 2$^b$ | 1.40 |
| Dispersant$^c$ | 2.10 |
| Aromatic 200$^e$ | 68.58 |

$^a$An emulsifier consisting of 64% of an anionic calcium salt of dodecylbenzene sulfonate, 16% of a nonionic 6-molar ethylene oxide condensation product of nonylphenol, and 20% butanol (Whitco Chemical Corp., Organics Div., New York, NY)

$^b$An emulsifier consisting of 56% of an anionic calcium salt of dodecylbenzene sulfonate, 24% of a nonionic 30-molar ethylene oxide condensation product of nonylphenol, and 20% butanol (Whitco Chemical Corp., Organics Div., New York, NY)

$^c$A dispersant consisting of a nonionic paste of 100% polyalkylene glycol ether (Union Carbide Chemical and Plastics Co. Inc., Danbury, CT)

$^d$B.P. 156-167° C. (Exxon Chemical Co., Houston, Texas)

$^e$B.P. 231-233° C. (Exxon Chemical Co., Houston, Texas)

Of these latter two solvents, the second formulation, which was less phytotoxic, is preferred.

The formulations of the 2,4-D and sulfonylurea components described in the tables are all well-known to those skilled in the art, and are commercially available materials which may be routinely mixed with the above Compound P formulations at desired ratios and dilutions, desirably with water, necessary to obtain the application rates specified in the tables.

It will be apparent that various modifications may be made in the formulations and applications of the compositions of this invention without departing from the inventive concepts herein as defined in the claims.

TABLE I

Weed Control by Compound P Alone and in Combination with Express ®$^{(a)}$ and Harmony ®$^{(b)}$ Herbicides Evaluated 23 Days after Treatment

| | Cpd. P Alone | | Express | | | | | | Harmony | | | | | |
|---|---|---|---|---|---|---|---|---|---|---|---|---|---|---|
| | | | Alone | | Comb. | | | | Alone | | Comb. | | | |
| Weed Species Appln. Rate$^{(c)}$ | L | H | L | H | LL | LH | HL | HH | L | H | LL | LH | HL | HH |
| | | | | | Percent Control | | | | | | | | | |
| Redroot Pigweed | 95 | 100 | 82 | 89 | 95 | 100 | 99 | 100 | 100 | 100 | 100 | 100 | 100 | 100 |
| Giant Ragweed | 30 | 55 | 56 | 65 | 54 | 68 | 58 | 63 | 83 | 86 | 84 | 88 | 83 | 91 |
| Common Lambsquarter | 68 | 94 | 100 | 100 | 98 | 100 | 98 | 100 | 100 | 99 | 99 | 100 | 100 | 100 |
| Wild Sunflower | 56 | 78 | 84 | 93 | 78 | 90 | 79 | 95 | 100 | 100 | 100 | 100 | 100 | 100 |
| Kochia | 64 | 83 | 98 | 100 | 78 | 99 | 96 | 96 | 90 | 93 | 93 | 100 | 97 | 99 |
| Wild Buckwheat | 48 | 61 | 64 | 50 | 41 | 80 | 68 | 80 | 92 | 96 | 95 | 100 | 97 | 99 |
| Russian Thistle | 66 | 87 | 100 | 100 | 94 | 100 | 88 | 98 | 100 | 100 | 99 | 100 | 99 | 99 |
| Wild Mustard | 24 | 31 | 99 | 98 | 81 | 99 | 89 | 99 | 75 | 86 | 74 | 84 | 80 | 84 |
| Wild Garlic | 54 | 69 | 73 | 83 | 78 | 88 | 74 | 86 | 96 | 94 | 88 | 94 | 90 | 93 |

| Compound | Application Rate$^{(c)}$ | |
|---|---|---|
| | Low Rate (L) | High Rate (H) |
| Compound P | 0.008 | 0.015 |
| Express | 0.004 | 0.008 |
| Harmony | 0.008 | 0.015 |

L = Low rate
H = High Rate
LL = Low rate of Cpd. P + low rate of standard
LH = Low rate of Cpd. P + high rate of standard
HL = High rate of Cpd. P + low rate of standard
HH = High rate of Cpd P + high rate of standard $^{(a)}$Express: methyl 2-[[[[N-(4-methoxy-6-methyl-1,3,5-triazin-2-yl)methylamino]carbonyl]amino]sulfonyl]benzoate (tribenuronmethyl) (DuPont, Wilmington, Del.)

$^{(b)}$Harmony: methyl 3-[[[[(4-methoxy-6-methyl-1,3,5-triazin-2-yl)amino]carbonyl]amino]sulfonyl]-2-thiophenecarboxylate (thifensulfuronmethyl) (DuPont, Wilmington, Del.)

$^{(c)}$Rate of application is in pounds of active ingredient/acre (lb/a)

TABLE II

Percent Weed Control by Compound P Alone and in Combination with Express ® Herbicide in Winter Barley and Winter Wheat Evaluated 22 Days After Treatment

| Weed Species | Cpd. P (7 g/ha)$^{(a)}$ | Express (19 g/ha) | Cpd. P + Express (7 + 19 g/ha) |
|---|---|---|---|
| Catchweed Bedstraw | 100 | 65 | 97 |

TABLE II-continued

Percent Weed Control by Compound P Alone and in Combination with Express ® Herbicide in Winter Barley and Winter Wheat Evaluated 22 Days After Treatment

| Weed Species | Cpd. P (7 g/ha)[a] | Express (19 g/ha) | Cpd. P + Express (7 + 19 g/ha) |
|---|---|---|---|
| Red Deadnettle | 93 | 97 | 100 |
| Wild Chamomile | 97 | 97 | 97 |
| Field Forget-Me-Not | 95 | 97 | 100 |
| Corn Poppy | 61 | 99 | 95 |
| Common Chickweed | 99 | 100 | 100 |
| Ivyleaf Speedwell | 92 | 92 | 97 |
| Persian Speedwell | 65 | 85 | 97 |
| Field Violet | 65 | 90 | 97 |

TABLE III

Percent Weed Control by Compound P Alone and in Combination with Ally ®[b] Herbicide Evaluated 30 Days After Treatment

| Herbicide | Rate g/ha[a] | Pineappleweed | Field Violet | Mouseearcress | Blackgrass | Common Chickweed | Ivyleaf Speedwell | Prostate Knotweed |
|---|---|---|---|---|---|---|---|---|
| Cpd. P | 10 | 19 | 0 | 0 | 0 | 69 | 96 | 99 |
|  | 15 | 25 | 10 | 0 | 0 | 71 | 99 | 99 |
|  | 30 | 39 | 17 | 14 | 0 | 81 | 100 | 100 |
|  | 60 | 56 | 36 | 25 | 0 | 86 | 100 | 100 |
| Ally | 3 | 34 | 0 | 0 | 0 | 81 | 7 | 95 |
| Cpd. P + Ally | 15 + 3 | 53 | 47 | 33 | 0 | 89 | 100 | 100 |

[a]Rate of application is in grams of active ingredient/hectare (g/ha)
[b]Ally: methyl 2-[[[[(4-methoxy-6-methyl-1,3,5-triazin-2-yl)amino]carbonyl]amino]sulfonyl]benzoate (metsulfuronmethyl) (DuPont, Wilmington, Del.)

TABLE IV

Postemergence Wheat Tolerance (Percent Injury) of Compound P Alone and in Combination with Ally ® Herbicide 7 Days After Treatment and Weed Control 30 Days After Treatment

| Herbicide | Rate g/ha[a] | PI[b] To Wheat | Catchweed Bedstraw | Field Violet | Persian Speedwell | Common Chickweed | Field-Forget-Me-Not | Cutleaf Cranesbill | Red Deadnettle | Ivyleaf Speedwell |
|---|---|---|---|---|---|---|---|---|---|---|
| Cpd. P | 7.5 | 1 | 78 | 13 | 10 | 10 | 13 | 30 | 8 | 15 |
|  | 15 | 4 | 89 | 11 | 12 | 6 | 7 | 10 | 13 | 69 |
|  | 30 | 8 | 96 | 45 | 12 | 9 | 5 | 10 | 8 | 89 |
| Ally | 6 | 0 | 14 | 79 | 74 | 78 | 55 | 73 | 64 | 0 |
| Cpd. P + Ally | 7.5 + 6 | 1 | 67 | 81 | 67 | 73 | 53 | 80 | 54 | 30 |
|  | 15 + 6 | 3 | 79 | 92 | 86 | 89 | 83 | 93 | 82 | 81 |

[a]Rate of application is in grams of active ingredient/hectare (g/ha).
[b]PI is percent injury to wheat.

TABLE V

Percent Control of Weeds and Tolerance of Wheat (Percent Injury) with Compound P Alone and in Combination with Ally ® Herbicide

| Herbicide | Rate g/ha[a] | Percent Injury to Wheat 7 DAT[b] | White Mustard 30 DAT | Persian Speedwell 30 DAT | Catchweed Bedstraw 30 DAT |
|---|---|---|---|---|---|
| Cpd. P | 10 | 2 | 71 | 91 | 90 |
|  | 15 | 4 | 90 | 95 | 92 |
|  | 30 | 6 | 95 | 99 | 96 |
|  | 60 | 12 | 99 | 99 | 98 |
| Ally | 3 | 0 | 35 | 69 | 25 |
| Cpd. P + Ally | 15 + 3 | 4 | 98 | 99 | 97 |

[a]Rate of application is in grams of active ingredient/hectare (g/ha).
[b]Represents days after treatment.

TABLE VI

Percent Weed Control and Percent Wheat Discoloration by Compound P Alone and in Combination with Ally ® Herbicide in Spring Wheat Evaluated 7 and 21 Days After Treatment

| Herbicide | Rate lb/a[a] | PD[b] in Spring Wheat 7 | Redroot Pigweed 21 | Common Lambsquarters 21 | Tansymustard 21 | Kochia 21 | Wild Buckwheat 21 | Russian Thistle 21 |
|---|---|---|---|---|---|---|---|---|
| Cpd. P | 0.015 | 2 | 43 | 45 | 95 | 23 | 43 | 25 |
|  | 0.031 | 4 | 63 | 80 | 100 | 45 | 50 | 43 |
| Ally | 0.002 | 0 | 90 | 10 | 100 | 10 | 65 | 30 |
| Cpd. P + Ally | 0.015 + 0.002 | 3 | 90 | 55 | 100 | 33 | 40 | 50 |
|  | 0.031 + 0.002 | 3 | 84 | 75 | 100 | 38 | 80 | 53 |

[a]Rate of application is in pounds of active ingredient/acre (lb/a).
[b]PD is percent discoloration in wheat.

TABLE VII

Percent Weed Control by Compound P Alone and in Combination with Ally ® Herbicide in Spring Wheat
Evaluated 30 Days After Treatment

| Herbicide | Rate lb/a[a] | Percent Control | | | | | | | | | | |
|---|---|---|---|---|---|---|---|---|---|---|---|---|
| | | Redroot Pigweed | Common Ragweed | Wild Sunflower | Common Marshelder | Kochia | Wild Buckwheat | Pennsylvania Smartweed | Russian Thistle | Wild Mustard | Velvetleaf | Common Lambsquarters |
| Cpd. P | 0.031 | 87 | 0 | 92 | 98 | 89 | 40 | 10 | 86 | 54 | 95 | 97 |
| | 0.063 | 96 | 3 | 95 | 98 | 96 | 75 | 13 | 95 | 60 | 99 | 100 |
| Cpd. P + Ally | 0.031 + 0.002 | 92 | 13 | 97 | 98 | 91 | 33 | 99 | 89 | 98 | — | — |

[a]Rate of application is in pounds of active ingredient/acre (lb/a).

Tables VIII and IX (below) demonstrate the improved effect obtained in controlling weeds in post-emergence spring and winter wheat by combining 2,4-dichlorophenoxy acetic acid ethyl ester ("2,4-D ester") with Compound P, as compared with the effect of either component alone.

In Tables VIII and IX the expected synergistic effect was calculated as follows, using the Compound P observed values at 0.031 lb./a, and the 2,4-D observed values at 0.50 lb./a:

$$\text{Expected} = \text{Cmpd } P \text{ (obs.)} + \frac{2,4\text{-D (obs.)}(100 - \text{Cmpd } P \text{ (obs)})}{100}$$

In these two tables (VIII and IX) the formulations employed comprised for Compound P a 2.0 lb/gal. emulsifiable concentrate; and for the 2,4-D ethyl ester a commercially available emulsifiable concentrate, each diluted to obtain the indicated application rates.

TABLE VIII

PERCENT CONTROL OF WEEDS IN WINTER WHEAT WITH A CMPD P COMBINATION WITH 2,4-D ISOOCTYL ESTER 15 DAYS AND 30 DAYS AFTER TREATMENT

| Plant Species | CMPD P Applied Alone at 0.031 lb/a Observed | CMPD P Applied Alone at 0.063 lb/a Observed | 2,4-D Ethyl Ester Applied Alone at 0.5 lb/a Observed | CMPD P Applied at 0.031 lb/a in Combination with 2,4-D Ethyl Ester Applied at 0.25 lb/a | |
|---|---|---|---|---|---|
| | | | | Observed | Expected |
| 15 DAYS AFTER TREATMENT | | | | | |
| Common Ragweed | 0* | 1 | 67 | 99 | 67 |
| Shepardspurse | 30 | 95 | 15 | 87 | 41 |
| Bittercress | 35 | 83 | 17 | 90 | 46 |
| Sticky Chickweed | 17 | 20 | 0 | 25 | 17 |
| Common Lambsquarter | 59 | 89 | 74 | 100 | 89 |
| Blue Mustard | 68 | 81 | 32 | 89 | 78 |
| Field Bindweed | 62 | 96 | 15 | 95 | 68 |
| Tansymustard | 45 | 51 | 58 | 93 | 77 |
| Flixweed | 80 | 94 | 23 | 94 | 85 |
| Bushy Wallflower | 82 | 96 | 29 | 92 | 87 |
| Pennsylvania Smartweed | 16 | 39 | 16 | 80 | 29 |
| Common Groundsel | 40 | 49 | 9 | 73 | 45 |
| Common Chickweed | 5 | 12 | 5 | 50 | 10 |
| Field Pennycress | 94 | 96 | 94 | 98 | 100 |
| Velvetleaf | 99 | 100 | 97 | 100 | 100 |
| 30 DAYS AFTER TREATMENT | | | | | |
| Shepardspurse | 93 | 98 | 20 | 97 | 94 |
| Bittercress | 90 | 95 | 77 | 95 | 98 |
| Smallseed Falseflax | 57 | 88 | 51 | 86 | 79 |
| Blue Mustard | 51 | 64 | 43 | 96 | 72 |
| Tansymustard | 68 | 63 | 88 | 100 | 96 |
| Flixweed | 79 | 91 | 39 | 99 | 87 |
| Bushy Wallflower | 90 | 98 | 45 | 97 | 95 |
| Field Pennycress | 98 | 99 | 99 | 99 | 100 |
| Common Groundsel | 33 | 44 | 11 | 85 | 40 |
| Common Chickweed | 10 | 30 | 5 | 30 | 15 |
| White Clover | 100 | 95 | 37 | 90 | 100 |
| Sticky Chickenweed | 40 | 10 | 5 | 24 | 43 |
| Common Lambsquarter | 60 | 89 | 93 | 100 | 97 |
| Field Bindweed | 33 | 84 | 53 | 83 | 69 |
| Pennsylvania Smartweed | 25 | 73 | 15 | 92 | 36 |
| Velvetleaf | 98 | 99 | 81 | 97 | 100 |
| Winter Wheat | 4 | — | 1 | 12 | 5 |

TABLE IX

PERCENT CONTROL OF WEEDS IN SPRING WHEAT WITH A CMPD P COMBINATION WITH 2,4-D ISOOCTYL ESTER 15 DAYS AND 30 DAYS AFTER TREATMENT

| Plant Species | CMPD P Applied Alone at 0.031 lb/a Observed | CMPD P Applied Alone at 0.063 lb/a Observed | 2,4-D Ethyl Ester Applied Alone at 0.5 lb/a Observed | CMPD P Applied at 0.031 lb/a in Combination with 2,4-D Ethyl Ester Applied at 0.25 lb/a | |
|---|---|---|---|---|---|
| | | | | Observed | Expected |
| *15 DAYS AFTER TREATMENT* | | | | | |
| Redroot Pigweed | 82* | 95 | 27 | 96 | 87 |
| Common Ragweed | 0 | 1 | 45 | 99 | 45 |
| Wild Sunflower | 85 | 91 | 88 | 88 | 98 |
| Common Marchelder | 91 | 90 | 79 | 95 | 98 |
| Kochia | 80 | 90 | 47 | 95 | 89 |
| Wild Buckwheat | 35 | 85 | 73 | 93 | 83 |
| Pennsylvania Smartweed | 9 | 9 | 25 | 62 | 32 |
| Russian Thistle | 73 | 88 | 36 | 94 | 83 |
| Common Lambsquarter | 100 | 100 | 98 | 100 | 100 |
| Velvetleaf | 99 | 100 | 96 | 100 | 100 |
| *30 DAYS AFTER TREATMENT* | | | | | |
| Redroot Pigweed | 87 | 96 | 60 | 96 | 95 |
| Common Ragweed | 0 | 3 | 95 | 100 | 95 |
| Wild Sunflower | 92 | 95 | 97 | 92 | 100 |
| Common Marchelder | 98 | 98 | 98 | 97 | 100 |
| Kochia | 89 | 96 | 71 | 95 | 97 |
| Wild Buckwheat | 40 | 75 | 71 | 83 | 52 |
| Pennsylvania Smartweed | 10 | 13 | 24 | 50 | 32 |
| Russian Thistle | 86 | 95 | 73 | 96 | 96 |
| Common Lambsquarter | 97 | 100 | 91 | 99 | 100 |
| Wild Mustard | 54 | 60 | 98 | 98 | 99 |
| Velvetleaf | 95 | 99 | 78 | 97 | 99 |
| Spring Wheat | 2 | — | 0 | 10 | 2 |

TABLE X

Weed Species Used in These Tests

| Common Name | Scientific Name |
|---|---|
| Redroot Pigweed | *Amaranthus retroflexus* |
| Giant Ragweed | *Ambrosia trifida* |
| Common Lambsquarters | *Chenopodium album* |
| Wild Sunflower | *Helianthus sp* |
| Kochia | *Kochia scoperia* |
| Wild Buckwheat | *Polygonum convolvulus* |
| Russian Thistle | *Salsola Kali* |
| Wild Mustard | *Brassica Kaber* |
| Wild Garlic | *Allium vineale* |
| Catchweed Bedstraw | *Galium aparine* |
| Red Deadnettle | *Lamium purpureum* |
| Wild Chamomile | *Matricaria chamomilla* |
| Field Forget-me-not | *Myosotis arvensis* |
| Corn Poppy | *Papaver rhoeas* |
| Common Chickweed | *Stellaria media* |
| Ivyleaf Speedwell | *Veronica hederaefolia* |
| Persian Speedwell | *Veronica persica* |
| Field Violet | *Viola arvensis* |
| Pineappleweed | *Matricaria matricarioides* |
| Mouseearcress | *Arabiodopsis thaliana* |
| Blackgrass | *Alopecurus myosuroides* |
| Prostate Knotweed | *Polygonum aviculare* |
| Cutleaf Cranesbill | *Geranium dissectum* |
| White Mustard | *Brassica hirta* |
| Tansymustard | *Descurainia pinnata* |
| Deadnettles | *Lamium sp* |
| Ryegrasses | *Lolium sp.* |
| Common Ragweed | *Ambrosia artemisiifolia* |
| Common Marshelder | *Iva xanthiafolia* |
| Pennsylvania Smartweed | *Polygonum pensylvanicum* |
| Velvetleaf | *Abutilon theophrasti* |

From the above results in Tables I–IX it will be seen that generally, the combinations of Compound P with the herbicides disclosed herein do provide a broader spectrum of weed control than do each of the herbicides when tested alone. A brief discussion of the tables of data follows:

In Table I, the combination of Compound P and Express herbicide provides greater control of wild buckwheat than either Compound P or Express herbicide when applied alone. The combination of Compound P and Harmony herbicide broadens the spectrum of activity of Compound P to include improved control of giant ragweed, wild sunflower, wild buckwheat, wild mustard, and wild garlic.

In Table II, the combination of Compound P and Express herbicide provides greater control of corn poppy in winter wheat and winter barley than does Compound P alone. In addition, the combination of Compound P and Express herbicide provides greater control of persian speedwell and field violet than either compound when applied alone.

In Table III, the combination of Compound P and Ally herbicide provides greater control of pineappleweed, field violet, and mouseearcress than either Compound P or Ally herbicide alone.

In Table IV, the combination of Compound P and Ally herbicide appears to be particularly efficacious. The combination provides greater control of nearly all of the weed species (i.e. field violet, persian speedwell, common chickweed, field forget-me-not, cutleaf cranesbill, red deadnettle, and ivyleaf speedwell) than does either Compound P or Ally herbicide alone. The combination of Compound P and Ally herbicide provides greater than 75% control of all of the weed species in these trials.

In Table V, the combination of Compound P and Ally herbicide provides nearly 100% control of persian speedwell and white mustard up to about 65 days.

Also, in Table V, the data shows that the combination of Compound P and Ally herbicide is essentially not phytotoxic to wheat.

In Table VI, the combination of Compound P and Ally herbicide broadens the spectrum of activity of both compounds as compared to each when applied alone. The combination, again is essentially not phytotoxic to spring wheat.

In Table VII, the combination of Compound P and Ally herbicide greatly increases the control of Pennsylvania smartweed and wild mustard as compared to the control shown by Compound P when applied alone.

In Tables VIII and IX, Compound P and the 2,4-D ester were tested alone and in combination. The combinations provided a clear showing of synergism as evidenced by the comparison of the observed control from the combination with the expected (calculated) control, shown in the last two columns of Tables VIII and IX. Note especially the results for:

common ragweed, shepherdspurse, bittercress, field bindweed, tansymustard, flixweed, Pennsylvania smartweed, and common groundsel, at 15 days after treatment in Table VIII;

for blue mustard, flixweed, common groundsel, field bindweed, and Pennsylvania smartweed, at 30 days after treatment in Table VIII;

for redroot pigweed, common ragweed, wild buckwheat, Pennsylvania smartweed, and russian thistle, at 15 days after treatment in Table IX; and for wild buckwheat, at 30 days after treatment in Table IX.

We claim:

1. A synergistic herbicidal composition comprising a herbicidally effective amount of the combination of:

(1) a triazolinone of the formula

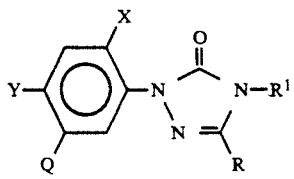

in which

R is halogen or lower alkyl;

$R^1$ is haloalkyl;

X is hydrogen, halogen, alkyl, haloalkyl, alkoxy or nitro;

Y is hydrogen, halogen, alkyl, haloalkyl, alkoxy, haloalkyl, halo lower alkylsulfinyl, or halo lower alkoxy;

Q is $-CH(R^2)C(R^3)(R^4)Q'$ or $-CH=C(R^4)Q'$;

$R^2$ is H or halogen;

$R^3$ is halogen;

$R^4$ is H or lower alkyl;

Q' is $CO_2H$, $CO_2R^5$, $CON(R^6)(R^7)$, CN, CHO, or $C(O)R^5$;

$R^5$ is alkyl, alkoxycarbonylalkyl, cycloalkyl, benzyl, chlorobenzyl, alkylbenzyl, or haloalkylbenzyl; and each of $R^6$ and $R^7$ is independently H, or a radical which is an alkyl, cycloalkyl, alkenyl, alkynyl, alkoxy, phenyl, benzyl, or $SO_2R^6$ (in which $R^6$ is other than H) or is one of said radicals substituted by halogen, alkyl, or cyano;

or a base-addition salt of the compound in which Q' is $CO_2H$; with the proviso that any alkyl, alkenyl, or alkynyl moiety have less than 6 carbon atoms and that any cycloalkyl moiety have 3 to 7 carbon atoms, and (2) dichloro- or chloro-lower alkylphenoxy lower alkanoic acids, or their corresponding herbicidally effective esters, or alkali metal or ammonium salts, in admixture with a suitable carrier.

2. The composition of claim 1 comprising a triazolinone of the formula

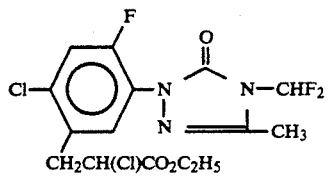

and a dichloro- or chloro-lower alkylphenoxy lower alkanoic acid or its corresponding herbicidally effective ester, or alkali metal or ammonium salts in admixture with a suitable carrier.

3. The composition of claim 2 wherein the phenoxy alkanoic acid is 2,4-D.

4. The composition of claim 2 wherein the phenoxy alkanoic acid is 2,4-D ammonium salt.

5. The composition of claim 2 wherein the phenoxy alkanoic acid is MCPA ammonium salt.

6. The composition of claim 2 wherein the phenoxy alkanoic acid is $MCPP_p$.

7. A method for controlling undesired plant growth which comprises applying to the locus where control is desired a herbicidally effective amount of the composition of claim 1.

8. A method for controlling undesired plant growth which comprises applying to the locus where control is desired a herbicidally effective amount of the composition of claim 2.

9. A method for controlling undesired plant growth which comprises applying to the locus where control is desired a herbicidally effective amount of the composition of claim 3.

10. A method for controlling undesired plant growth which comprises applying to the locus where control is desired a herbicidally effective amount of the composition of claim 4.

11. A method for controlling undesired plant growth which comprises applying to the locus where control is desired a herbicidally effective amount of the composition of claim 5.

12. A method for controlling undesired plant growth which comprises applying to the locus where control is desired a herbicidally effective amount of the composition of claim 6.

* * * * *